(12) United States Patent
Pastrello et al.

(10) Patent No.: US 8,677,930 B2
(45) Date of Patent: Mar. 25, 2014

(54) UNIT FOR MAKING ABSORBENT NAPPY/DIAPER PADS

(75) Inventors: Gabriele Pastrello, Milan (IT); Aldo Fusarpoli, Offanengo (IT); Matteo Piantoni, Albino (IT); Goeran Forsbring, Kungsbacka (SE); Robert Perneborn, Goeteborg (SE)

(73) Assignee: GDM S.p.A. (IT)

( * ) Notice: Subject to any disclaimer, the term of this patent is extended or adjusted under 35 U.S.C. 154(b) by 25 days.

(21) Appl. No.: 13/201,796

(22) PCT Filed: Mar. 8, 2010

(86) PCT No.: PCT/IB2010/050986
§ 371 (c)(1),
(2), (4) Date: Aug. 16, 2011

(87) PCT Pub. No.: WO2010/103453
PCT Pub. Date: Sep. 16, 2010

(65) Prior Publication Data
US 2011/0297080 A1 Dec. 8, 2011

(30) Foreign Application Priority Data
Mar. 9, 2009 (IT) .............................. BO2009A0140

(51) Int. Cl.
*B05C 5/00* (2006.01)
*B05C 19/00* (2006.01)
*B05B 13/02* (2006.01)

(52) U.S. Cl.
USPC ............ 118/504; 118/301; 118/308; 118/324

(58) Field of Classification Search
USPC ......... 118/308, 324, 301, 504, 505; 425/81.1, 425/82.1, 83.1; 156/62.2, 62.4; 137/625.15, 137/625.46
See application file for complete search history.

(56) References Cited

U.S. PATENT DOCUMENTS

| 4,800,102 A | 1/1989 | Takada |
| 6,033,199 A | 3/2000 | Vonderhaar et al. |
| 6,257,804 B1 | 7/2001 | Gathmann |
| 2011/0287170 A1* | 11/2011 | Colclough et al. ........... 427/2.31 |

FOREIGN PATENT DOCUMENTS

EP 0979682 2/2000

OTHER PUBLICATIONS

International Search Report and Written Opinion dated Jun. 10, 2010 from PCT application.

* cited by examiner

*Primary Examiner* — Yewebdar Tadesse
(74) *Attorney, Agent, or Firm* — Timothy J. Klima; Shuttleworth & Ingersoll, PLC

(57) ABSTRACT

Absorbent nappy/diaper pads composed of a first absorbent base material, and a second absorbent material consisting of superabsorbent polymer powders, are made by a unit (3) that comprises a conveyor (11) carrying the first absorbent material along a predetermined feed path (P), and a feed system (24) by which the superabsorbent polymer powders are released onto the feed path (P); the feed system (24) comprises a fixed duct (27) with an outlet (45) directed at the feed path (P), and a valve (34), positioned along an intermediate segment of the duct (27), by which the superabsorbent polymer powders are dispensed intermittently and controllably. The valve (34) comprises a rotating disc (41), set transversely to the duct (27), with an annular region (51) that revolves through a gap (43) in the duct (27) and presents at least one slot (42) delimited longitudinally, in the direction of rotation of the disc (41), by a leading edge (52) and a trailing edge (53); the radial dimension of the slot (42) increases progressively, at least along a part of the distance from the leading edge (52) toward the trailing edge (53).

15 Claims, 3 Drawing Sheets

UNIT FOR MAKING ABSORBENT NAPPY/DIAPER PADS

This application is the National Phase of International Application PCT/IB2010/050986 filed Mar. 8, 2010 which designated the U.S. and that International Application was published under PCT Article 21(2) in English.

This application claims priority to Italian Patent Application No. B02009A000140 filed Mar. 9, 2009 and PCT Application No. PCT/IB2010/050986 filed Mar. 8, 2010, which applications are incorporated by reference herein.

TECHNICAL FIELD

The present invention relates to a unit for making absorbent pads used in nappies, or diapers.

BACKGROUND ART

Conventionally, nappies (known also as diapers) comprise an absorbent pad sandwiched between a layer of non-woven fabric permeable to liquids, and a layer of impermeable material such as polyethylene. Also included, usually between the pad and the layer of non-woven fabric, is a fluid distribution layer, widely referred to as an acquisition layer, or acquisition-distribution layer (ADL).

Nappies are substantially rectangular in appearance, and present an anatomically contoured central section.

The pads likewise are of substantially rectangular outline, and aligned centrally on the nappy.

The aforementioned pads are formed generally in the aspirating pockets or cavities of a drum, rotatable about a horizontal axis and fed at a point on its periphery with a flow of absorbent material.

The flow of material consists predominantly of synthetic and/or natural fibrous particles and may also contain superabsorbent polymer (SAP) powders blended homogeneously with the fibrous particles.

In prior art units, the cylindrical surface of the drum on which the pads take shape is surmounted by a hood, occupying a sector of predetermined length, into which the flow of absorbent material is fed pneumatically from the top.

Likewise in prior art units, whether the flow of material contains fibrous particles only, or a blend of fibrous particles and superabsorbent polymer powders, the inside of the hood may also accommodate the outlet of a feed duct from which discrete quantities of superabsorbent polymer powders are dispensed.

The dispensing action is produced generally by intermittently operated valve means, and under pressure, in such a way that a circumscribed central area of the pad will be loaded with the SAP material.

In one prior art solution, such valve means take the form of a rotating disc furnished with one or more substantially rectangular arcuate openings through which the flow of SAP material is directed intermittently, as the disc rotates, through the feed duct and into the hood, and ultimately into the cavities of the drum in which the pads are formed.

Using the valve means described above, it is not possible to obtain a uniform distribution of the discrete quantities of SAP material within the circumscribed area of application.

Moreover, it is not possible to guarantee a precise geometrical shape for the circumscribed area of application when using such valve means.

DISCLOSURE OF THE INVENTION

The object of the present invention is to provide a unit for making absorbent pads in which the aforementioned discrete quantities of superabsorbent polymer powder material are uniformly distributed within their circumscribed area of application.

A further object of the invention is to provide a unit for making absorbent pads, by which discrete quantities of superabsorbent polymer powder material can be applied to a circumscribed area of precise geometrical shape on each successive pad.

The stated objects are realized according to the present invention in a unit for making absorbent pads, of which the features are as recited in one or more of the claims appended.

BRIEF DESCRIPTION OF THE DRAWINGS

The invention will now be described in detail, by way of example, with the aid of the accompanying drawings, in which.

DETAILED DESCRIPTION OF THE PREFERRED EMBODIMENTS OF THE INVENTION

Figure 1:
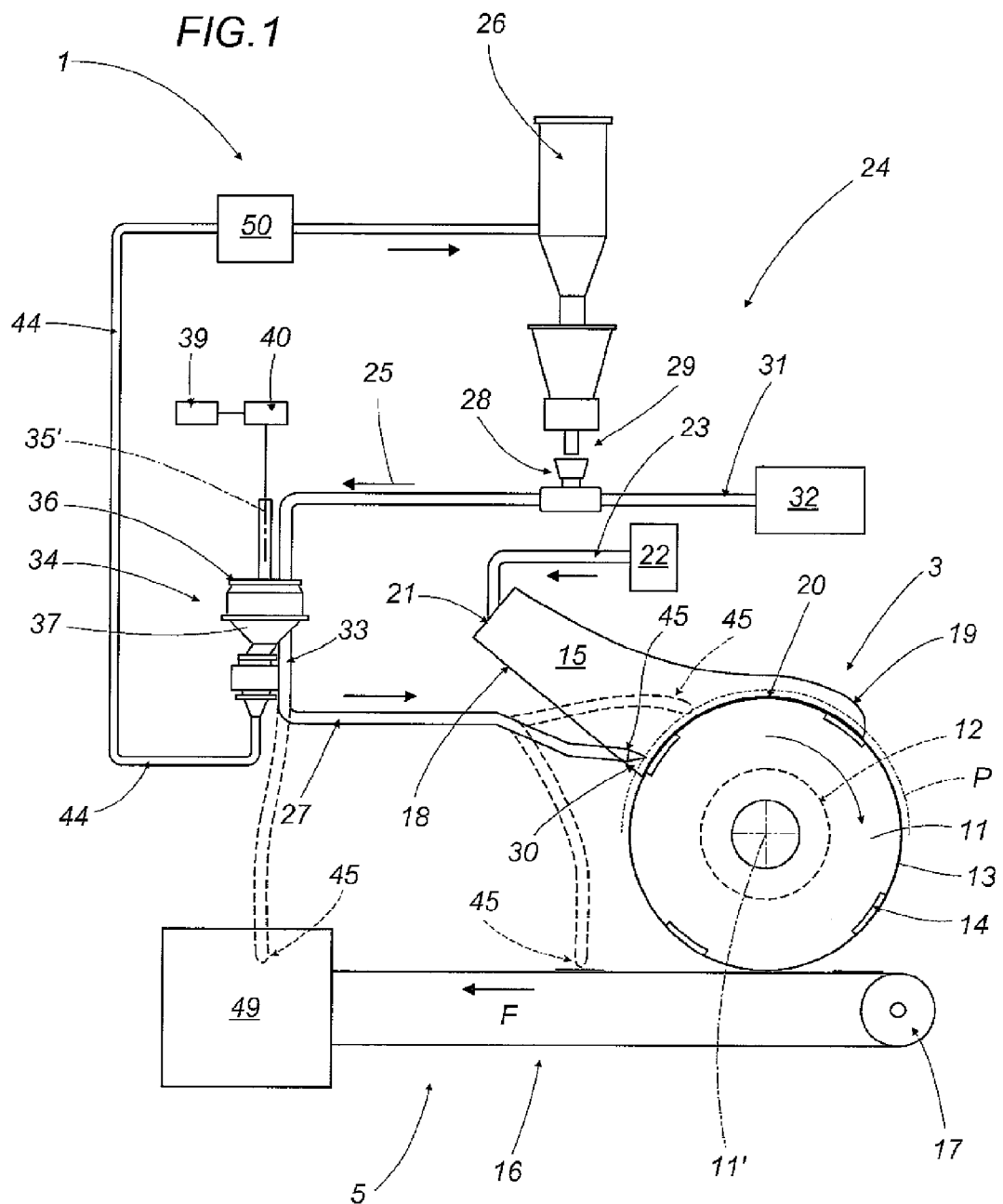
FIG. 1 is a schematic view of a machine comprising a unit for making absorbent nappy pads, embodied in accordance with the present invention.
Figure 2:
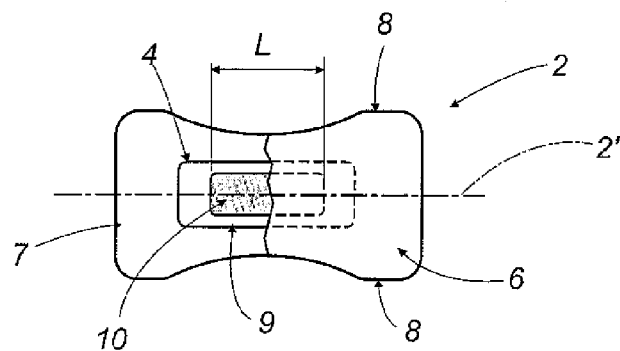
FIG. 2 is a plan view of a nappy comprising a pad of the type made by the unit illustrated in FIG. 1.

With reference to FIGS. 1 and 2, numeral 1 denotes a machine, in its entirety, for the manufacture of absorbent nappies, known also as diapers 2, comprising a unit 3 for making absorbent pads 4 and, connected to the outfeed of this same unit 3, a unit 5 by which the nappies 2 are assembled.

As illustrated to advantage in FIG. 2, the nappies 2 manufactured by the machine 1 comprise one of the aforementioned absorbent pads 4, sandwiched by the assembly unit 5 between a fluid-permeable layer or topsheet 6 of non-woven fabric, and a layer or backsheet 7 of impermeable material such as polyethylene.

The assembled nappy will also comprise an acquisition-distribution layer, or ADL (not illustrated in detail, being only incidental to the invention), located between the pad 4 and the layer 6 of non-woven fabric.

The nappies 2 are of substantially rectangular outline, aligned on a longitudinal axis denoted 2', with longitudinal side edges 8 and a central area anatomically contoured in familiar fashion.

The single pad 4, likewise generally rectangular and aligned centrally on the nappy 2, comprises a layer 9 of fibrous particles, produced from cellulose fibres for example, of which a substantially rectangular central portion 10 on the side facing the permeable topsheet 6 is loaded with superabsorbent polymer (SAP) powder material of the type mentioned previously.

The unit 3 comprises a conveyor 11 embodied as a drum, set in rotation about a horizontal axis 11' by actuator means 12 indicated schematically as a block, and turning clockwise as viewed in FIG. 1.

The cylindrical surface 13 of the drum 11 is fashioned with a plurality of aspirating cavities 14, appearing substantially rectangular in shape and equispaced angularly along a predetermined feed path P. The drum 11 is surmounted by a hood element 15, and positioned directly above a horizontal belt conveyor 16 looped around end rollers 17 and advancing substantially tangential to the selfsame drum 11 in the direction of the arrow denoted F.

The belt conveyor 16 forms part of the aforementioned assembly unit 5 and connects the drum 11 with devices schematized as a block, denoted 49, by which the nappies 2 are finished.

The hood 15 is delimited longitudinally by two walls 18 and 19, left and right respectively as viewed in FIG. 1, and positioned directly above the drum 11, combining with a sector of predetermined length presented by the cylindrical surface 13 to create a chamber 20 inside which the pads 4 are formed in the cavities 14. More exactly, referring to the direction of rotation of the drum 11, the left hand wall 18 is a rear wall of the hood 15, and the right hand wall 19 is a front wall of the hood 15.

The hood 15 presents an opening 21 at the top such as will admit feed means, schematized as a block denoted 22, supplying a first absorbent base material 23. The base material 23 consists predominantly of synthetic and/or natural fibrous particles. Alternatively, the base material 23 could also comprise superabsorbent polymer (SAP) powders, blended homogeneously with the synthetic and/or natural fibrous particles.

The unit 3 also comprises a feed circuit 24 by which a flow of a second absorbent material, consisting in discrete quantities of superabsorbent polymer (SAP) powders, can be supplied to the hood 15, hence to the feed path P.

The feed circuit 24 comprises a storage tank 26 containing the powders, and a fixed duct 27 connected by way of a funnel shaped inlet, denoted 28, to an outlet 29 of the tank 26. The fixed duct 27 terminates at a delivery end 30 located internally of the hood 15.

The inlet 28 of the circuit 24 is also connected by way of a further duct 31 to a source of compressed air, schematized as a block denoted 32.

Positioned along an intermediate and substantially vertical segment 33 of the fixed duct 27 are valve means 34, by which the SAP powders can be dispensed intermittently and controllably.

Figure 3:
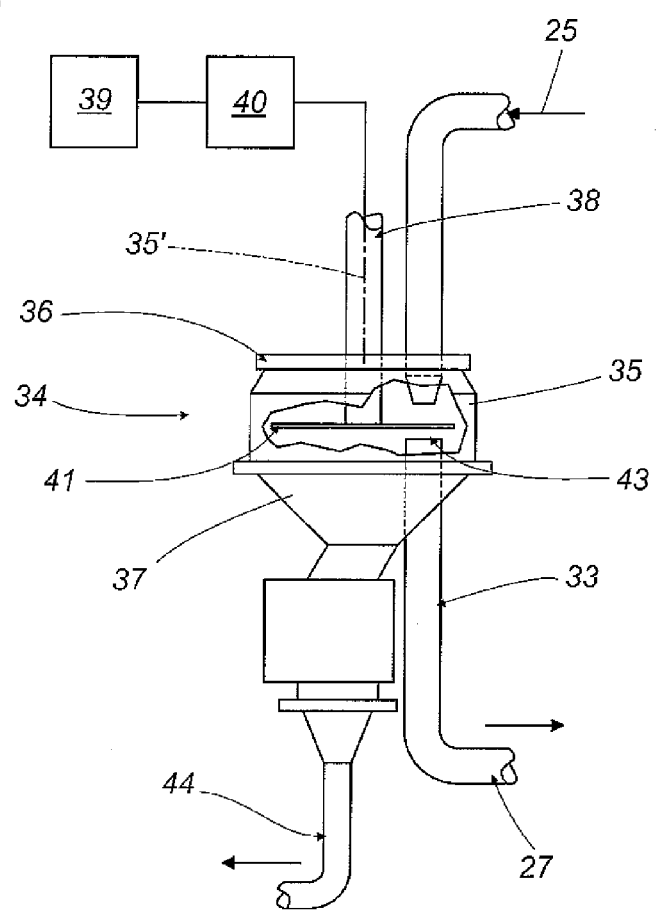
FIG. 3 shows a detail of the unit in FIG. 1, enlarged and cut away in part.

Referring to FIG. 3, in particular, the valve means 34 comprise a hollow cylindrical body 35 aligned on a vertical axis 35', delimited by a cover 36 uppermost, and a frustoconical closure element 37 beneath.

Numeral 38 denotes a vertical shaft aligned coaxially with the cylindrical body 35, of which the top end passes through the cover 36 and is connected to a motor 39 by way of coupling means 40.

Figure 4:
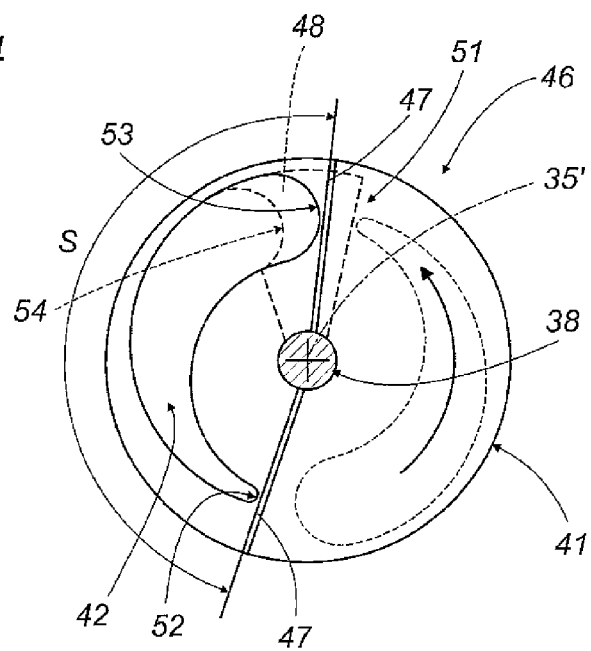
FIG. 4 shows a detail of FIG. 3, illustrated in a plan view.

Referring also to FIG. 4, the cylindrical body 35 houses a rotating disc 41 keyed to the vertical shaft 38 and constituting the primary component of the valve means 34. The disc 41 presents an opening or slot 42 of arcuate appearance and predetermined radial dimensions, of which the geometry will be described in due course, and of which the angular length, denoted S, is a function of the longitudinal dimension L selected for the central portion 10 of the pad 4 to be loaded with SAP material.

The vertical segment 33 of the duct 27 passes though the cover 36 and through the frustoconical closure element 37, and presents a gap 43 internally of the cylindrical body 35.

The disc 41, rotating about the vertical axis 35', is disposed at right angles to the vertical segment 33 of the duct 27 and positioned in such a way that an annular region 51 coinciding with the slot 42 revolves through the aforementioned gap 43.

The slot 42 is delimited longitudinally, along the direction of rotation of the disc 41, by a leading edge 52 and a trailing edge 53.

The radial dimension of the slot 42 increases from the leading edge 52 toward the trailing edge 53, at least along a portion of its angular length, and in particular, increases progressively to create a profile of substantially triangular outline.

In an alternative embodiment (not illustrated), an intermediate portion of the slot 42 might present a constant radial dimension. In this instance, the intermediate portion would be interposed between a leading portion of progressively increasing radial width, and a rear portion delimited by the trailing edge 53.

The two edges 52 and 53 are of semi-circular profile and, self-evidently, the radius of curvature of the trailing edge 53 will be greater than that of the leading edge 52.

The circuit 24 comprises a return duct 44 departing from the bottom of the frustoconical closure element 37 and connected to the tank 26.

Numeral 50 denotes pneumatic means of conventional type schematized as a block, installed on the return duct 44, by which the polymer powders are conveyed through the circuit.

The delivery end 30 of the fixed duct 27 presents an outlet 45, or nozzle, discharging internally of the chamber 20 at a point in close proximity to the feed path P; in effect, the outlet 45 will be positioned facing the feed path P, just a few centimeters distant. More exactly, the distance of the outlet 45 from the feed path P is advantageously less than 20 cm, and preferably less than 10 cm.

Furthermore, the outlet 45 is positioned close to the aforementioned rear wall 18 of the hood, so as to deposit the SAP powder material on the bottom of the cavities 14.

An alternative solution, indicated by phantom lines in FIG. 1, would be to place the outlet 45 at a substantially central point between the end walls 18 and 19 of the hood 15, so that the SAP powder material can be released into the cavities 14 when the selfsame cavities are already part-filled with the absorbent base material 23.

Referring to FIG. 4, the shaft 38 is set in rotation anticlockwise by the motor 39, turning continuously and in such a way that the disc 41 completes a full revolution of 360° about the vertical axis 35' as each cavity 14 of the drum 11 passes through the chamber 20 in which the pads 4 are formed.

Consequently, with each full revolution of the drum 11, the disc 41 completes a number of revolutions equal to the number of cavities 14.

During each full revolution of the disc 41, the valve means 34 assume an open configuration and a closed configuration as the gap 43 in the duct 27 is occupied respectively by the part of the disc 41 presenting the slot 42 and by the part of the disc having no slot. Importantly, it will be seen that by virtue of its shape, the slot 42 influences the quantity of powder directed into the cavities 14, rather than the shape of the central portion 10. The shape of this portion, conversely, is influenced by the substantially rectangular outline of the outlet 45 and its proximity to the feed path P.

In operation, absorbent base material 23 is directed by the feed means 22 into the chamber 20 through the opening 21 of the hood 15, and at the same time, the flow 25 of superabsorbent powder material generated by the source of compressed air 32 is directed through the valve means 34 and released by way of the outlet 45, likewise into the chamber 20.

The valve means 34 are timed to open, during the rotation of the drum 11, in such a way that the SAP powder material will be released by the outlet 45 as each cavity 14 advances through an arc of rotation of the drum 11 corresponding in length to the longitudinal dimension L of the rectangular central portion 10.

The disc 41, and the relative slot 42, of which at least the leading portion presents a radial dimension increasing progressively along the direction of rotation of the disc 41, together provide means 46 by which to regulate the flow 25 of SAP powder material in such a way that the central portions 10 of the pads 4 will present a uniform distribution of the powder material across their entire surface area.

In effect, with the valve means 34 in the closed configuration, an accumulation of SAP powder material occurs within the hollow cylindrical body 35 and above the disc 41.

Accordingly, the gradual widening of the slot 42 is designed to avoid the situation that when the valve means 34 open each time, the outlet 45 will release an excessive amount of the powder material, as occurs typically with prior art systems, resulting in the formation of pads 4 that present portions 10 loaded with SAP powder material non-uniformly across their entire surface area, and in particular, loaded to excess at one end with the superabsorbent powder.

It will be seen that with the outlet 45 positioned close to the rear wall 18 of the hood 15, the central portions 10 will be formed on a surface area of the pads 4.

In addition, since the outlet 45 is placed at a relatively short distance from the cylindrical surface 13 of the drum 11, and therefore from the bottom of the cavities 14 on their entry to the chamber 20, the central portion 10 assumes a well-defined shape, circumscribed and centred on the pad 4.

As discernible in FIG. 4, two fixed radial walls or baffles 47 are mounted perpendicularly to the disc 41, positioned externally of the slot 42 and compassing an angle of predetermined width. The baffles 47 in question serve to direct the excess SAP powder material toward the return duct 44, and ultimately back to the tank 26. In other words, the function of the baffles 47 is to engage the cloud of powder that forms on the disc 41 whenever the passage of the flow is prevented by the disc, and remove it mechanically. This is in order to prevent a quantity of SAP powder material greater than that desired from being directed into the section of the fixed duct 27 lying downstream of the gap 43, at the moment when the powder is allowed by the slot 42 to pass along the duct.

In FIG. 4, numeral 48 denotes a circular sector placed coaxially on top of the disc 41. The sector 48 functions as a masking element, rotatable about the axis 35' of the disc 41, such as can be used when necessary to alter the angular length S of the slot 42 and thus alter the longitudinal dimension L of the central portion 10. More exactly, the sector 48 serves to close off a part of the slot 42 near the trailing edge 53 and, advantageously, presents an edge 54 for this same purpose that is shaped identically to the trailing edge 53.

The angular position of the sector 48 can be adjusted manually, or alternatively, the sector can be motorized.

In an alternative solution, not illustrated but readily imaginable to a person skilled in the art, the masking element 48 is replaced by means for controlling the speed of rotation of the disc 41, such as will regulate the rate at which the slot 42 passes through the gap 43 in the duct 27 according to the selected length of the aforementioned longitudinal dimension L. Advantageously, the speed control means in question could take the form of an electronic cam such as will accelerate and decelerate the disc 41 appropriately when the slot 42 rotates externally of the gap 43. With this type of arrangement, the slot 42 can turn a full revolution with the passage of each successive cavity 14 while moving at a selected speed through the gap 43, regardless of the speed at which the machine 1 may be operating.

Figure 5:
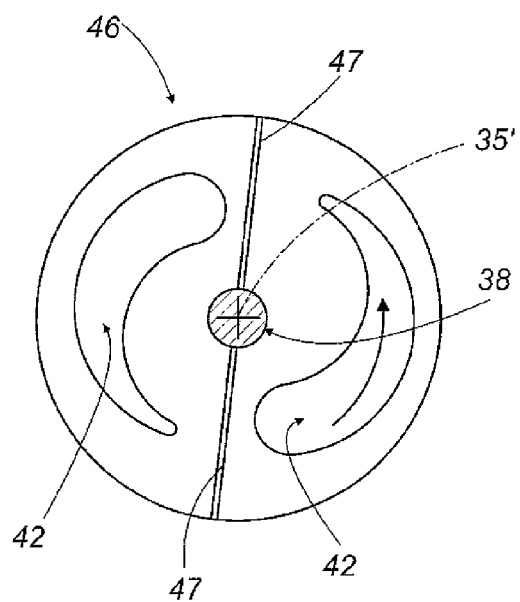
FIG. 5 shows the detail of FIG. 3, illustrated in an alternative embodiment.

In place of the single slot 42, the disc 41 of the valve means 34 might be furnished with a plurality of angularly equispaced slots, for example two such slots 42 as illustrated in FIG. 5.

In this instance, during each 360° revolution of the disc 41, the valve means 34 will assume the open configuration twice, feeding the SAP powder material to two successive cavities 14 in the course of their passage through the chamber 20.

It will be appreciated that, within the scope of the invention, the intermittently released SAP powder material might be applied directly to a nappy when already part assembled, before the pad is sandwiched between the backsheet and the acquisition-distribution layer or the topsheet. For example, employing the method described above, the intermittently released SAP powder material might be applied (see phantom lines) as the nappies 2 pass through the aforementioned finishing devices 49, schematized as a block in FIG. 1.

Likewise within the scope of the invention, a further solution might be to deposit the intermittently released SAP powder material (see phantom lines) at a point along the belt conveyor 16 of the assembly unit 5.

In short, the position of the outlet 45 can be selected advantageously, not only in relation to the drum 11 but also, and alternatively, in relation to the conveyor 16 or to the devices 49 by which the nappies 2 are finished, as illustrated in FIG. 1.

The invention claimed is:

1. A unit for making absorbent diaper pads composed of a first absorbent base material, and a second absorbent material including superabsorbent polymer powders, comprising:
   a conveyor mechanism by which the first absorbent material is directed along a predetermined feed path;
   a feed mechanism by which the superabsorbent polymer powders are released onto the feed path, comprising a fixed duct with an outlet directed at the path, and a valve mechanism positioned along an intermediate segment of the fixed duct, by which the superabsorbent polymer powders are dispensed intermittently and controllably;
   the valve mechanism comprising a rotating disc disposed transversely to the fixed duct and including an annular region revolving through a gap in the fixed duct;
   the annular region of the rotating disc including at least one slot having, along a direction of rotation of the rotating disc, a leading edge and a trailing edge establishing an angular length of the slot; and,
   a radial dimension of the at least one slot increasing from the leading edge toward the trailing edge, at least along a portion of the angular length;
   wherein the valve mechanism comprises a length altering mechanism for altering the angular length of the at least one slot for determining a longitudinal dimension of a portion of the absorbent diaper pad onto which the superabsorbent polymer powders are directed by the fixed duct.

2. A unit as in claim 1, wherein the radial dimension of the at least one slot increases progressively from the leading edge toward the trailing edge, at least along a portion of the angular length.

3. A unit as in claim 2, wherein the at least one slot includes a substantially triangular outline extending from the leading edge toward the trailing edge, at least along a portion of the angular length.

4. A unit as in claim 1, wherein the rotating disc is positioned at a right angle to the fixed duct.

5. A unit as in claim 1, wherein the rotating disc rotates about a vertical axis.

6. A unit as in claim 1, wherein the outlet is positioned in close proximity to the feed path.

7. A unit as in claim 1, wherein the length altering mechanism comprises a rotatable masking element adjustable for position about the axis of rotation of the rotating disk for adjustably masking an angular portion of the at least one slot to alter the angular length of the at least one slot.

8. A unit as in claim 7, wherein the rotatable masking element includes an edge that serves as a trailing edge of the at least one slot when masking the at least one slot, the edge having a same shape as the trailing edge.

9. A unit as in claim 1, wherein the valve mechanism comprises a controlling mechanism for controlling a speed of rotation of the rotating disc, to a rate at which the at least one slot passes through the gap in the fixed duct according to the longitudinal dimension.

10. A unit as in claim 1, wherein the conveyor mechanism comprises a device for forming and conveying the absorbent diaper pads, including a plurality of cavities in which the absorbent diaper pads are formed and conveyed along the feed path.

11. A unit as in claim 10, wherein the device for forming and conveying the absorbent diaper pads comprises a rotating drum including on a periphery of the rotating drum a plurality of angularly equispaced cavities in which the absorbent diaper pads are formed and conveyed along the feed path.

12. A unit as in claim 11, comprising a hood through which the first absorbent material is fed to the rotating drum, wherein the hood is positioned above the drum to create a chamber within which the absorbent diaper pads are formed in the cavities.

13. A unit as in claim 12, wherein the hood is delimited longitudinally by a front wall and a rear wall, as referred to the direction of rotation of the rotating drum, and the fixed duct terminates internally of the hood with a relative outlet positioned close to the rear wall.

14. A unit as in claim 12, wherein the hood is delimited longitudinally by a front wall and a rear wall, as referred to the direction of rotation of the rotating drum, and the fixed duct terminates internally of the hood with a relative outlet occupying a substantially central position between the front wall and the rear wall.

15. A unit as in claim 1, wherein the valve mechanism further comprises two fixed radial walls mounted perpendicularly to the rotating disc, positioned externally of the at least one slot and encompassing an angle of predetermined width.

* * * * *